(12) United States Patent
Sasaki et al.

(10) Patent No.: US 12,083,123 B2
(45) Date of Patent: Sep. 10, 2024

(54) METHOD FOR THE DETECTION OF DRUG-INDUCED ORGAN OR TISSUE INJURY IN IMPDH INHIBITOR TREATED PATIENTS

(71) Applicants: University of Cincinnati, Cincinnati, OH (US); Children's Hospital Los Angeles, Los Angeles, CA (US)

(72) Inventors: Atsuo Sasaki, Cincinnati, OH (US); Mikako Warren, Pasadena, CA (US)

(*) Notice: Subject to any disclaimer, the term of this patent is extended or adjusted under 35 U.S.C. 154(b) by 58 days.

(21) Appl. No.: 17/494,968

(22) Filed: Oct. 6, 2021

(65) Prior Publication Data

US 2022/0105099 A1    Apr. 7, 2022

Related U.S. Application Data

(60) Provisional application No. 63/088,106, filed on Oct. 6, 2020.

(51) Int. Cl.
*A61K 31/5377* (2006.01)
*A61P 1/16* (2006.01)
*G01N 33/50* (2006.01)

(52) U.S. Cl.
CPC .......... *A61K 31/5377* (2013.01); *A61P 1/16* (2018.01); *G01N 33/5008* (2013.01)

(58) Field of Classification Search
CPC .... A61K 31/5377; A61P 1/16; G01N 33/5008
See application file for complete search history.

(56) References Cited

PUBLICATIONS

Duann, et. al., Adv. Exp. Med. Biol. 2017; 982:529-551. (Year: 2017).*
Pizzorno, Joseph; Integrative Medicine*vol. 13,No. 2; Apr. 2014. (Year: 2014).*
Allison, et al., "Mecahnisms of Action of Mycophenolic Acid", Annals New York Academy of Sciences, pp. 63-87, 1996.
Demetris, et al., "Banff Schema for Grading Liver Allograft Rejection: An International Consensus Document", vol. 25, No. 3, pp. 658-663, Mar. 1997.
Clinical and Research Information on Drug-Induced Liver Injury: NCBI bookshelf: Azathioprine, pp. 1-29, Aug. 21, 2017.
Clinical and Research Information on Drug-Induced Liver Injury: NCBI bookshelf: Cyclophosphamide, pp. 1-12, Nov. 5, 2017.
Clinical and Research Information on Drug-Induced Liver Injury: NCBI bookshelf: Mercaptopurine, pp. 1-24, Aug. 17, 2017.
Fisher, et al., "Drug-Induced Liver Inquiry", Arch Pathol Lab Med., vol. 139, pp. 1-12, Jul. 2015.
Kofuji, et al., "IMP dehydrogenase-2 drives aberrant nuclear activity and promotes tumorigenesis in glioblastoma", Nat. Cell Biol., vol. 8, pp. 1-32, Aug. 21, 2019.
Mukherjee, et al., "A Comprehensive Review of Immunosuppression Used for Liver Transplant", Journal of Transplantation, vol. 2009, pp. 1-20, Jul. 2009.
Naffouje, et al., "Anti-Tumor Potential of IMP Dehydrogenase Inhibitors: A Century-Long Story", Cancers, vol. 11, pp. 1-30, 2019.

* cited by examiner

*Primary Examiner* — Jeffrey H Murray
(74) *Attorney, Agent, or Firm* — Dinsmore & Shohl LLP

(57) ABSTRACT

The present disclosure concerns methods of detecting injury to a tissue and/or organ in a subject. In some aspects, the subject is the recipient of a transplant, such as a liver transplant. In some aspects, the subject is undergoing treatment with an immunosuppressant. In some aspects, the present disclosure concerns the identification of aberrant mitochondria in the subject to identify injury to the tissue and/or organ of the subject. Detecting aberrant mitochondria allows for remedial and/or corrective action to prevent or avoid significant injury.

13 Claims, 11 Drawing Sheets

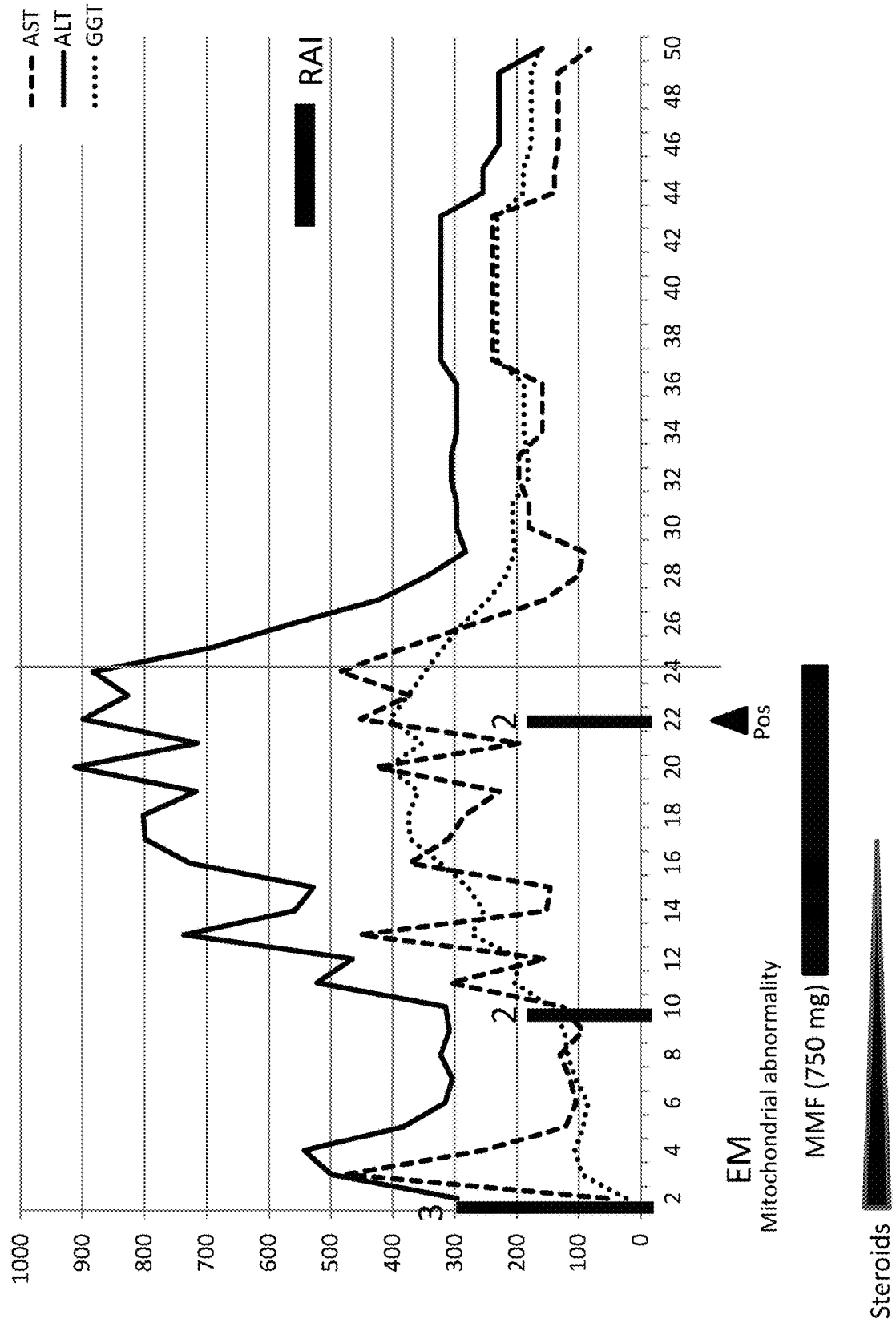

FIG. 3(cont.)
FIG. 3B
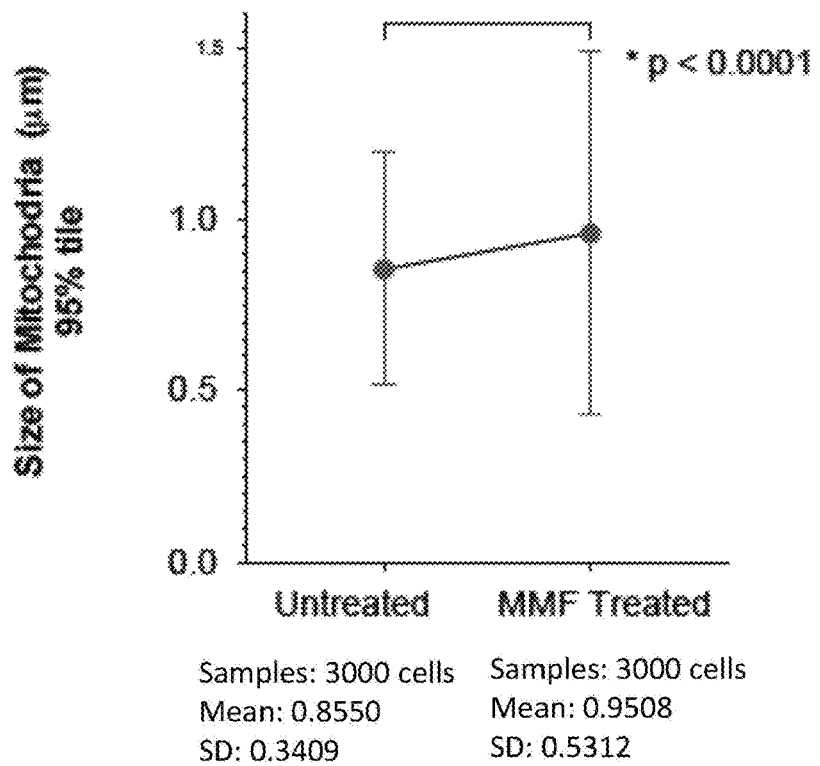
FIG. 3C
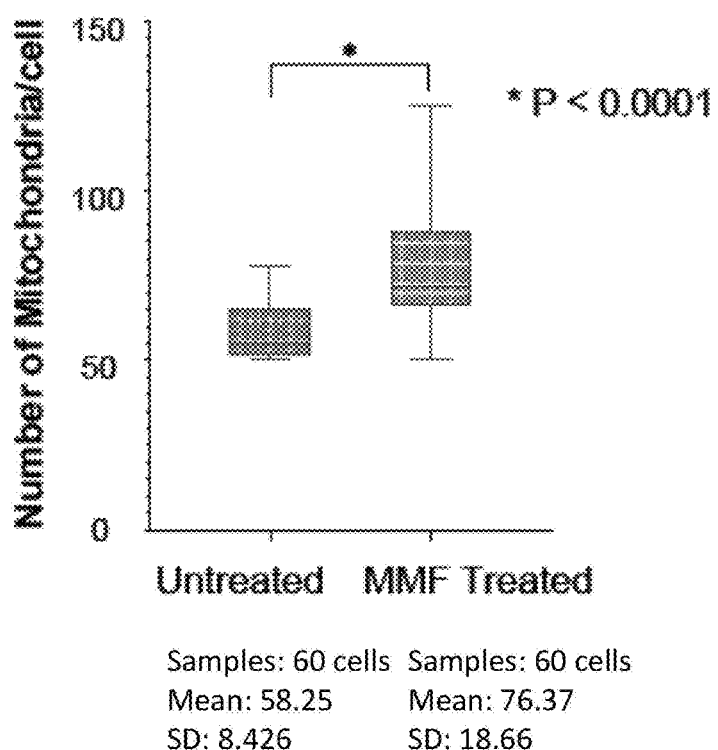

FIG. 6
FIG. 6A
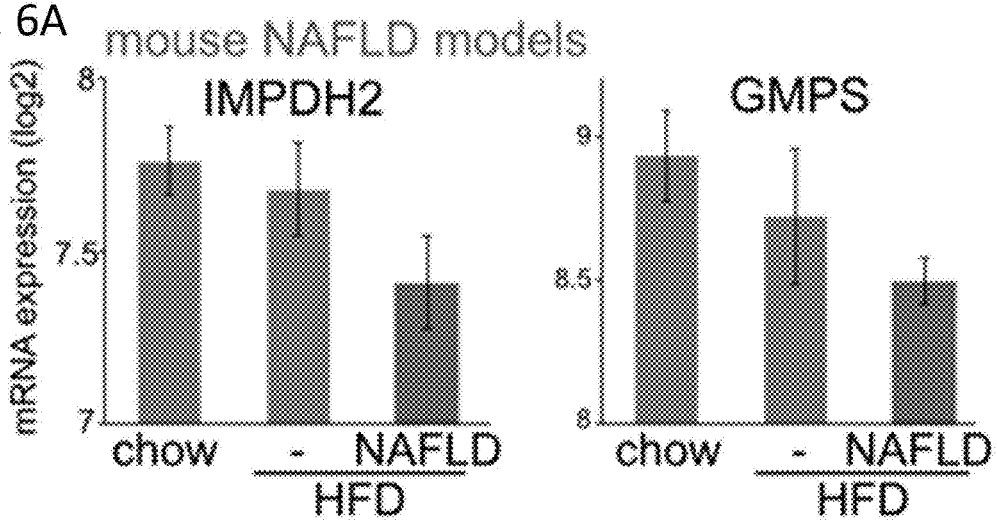
FIG. 6B
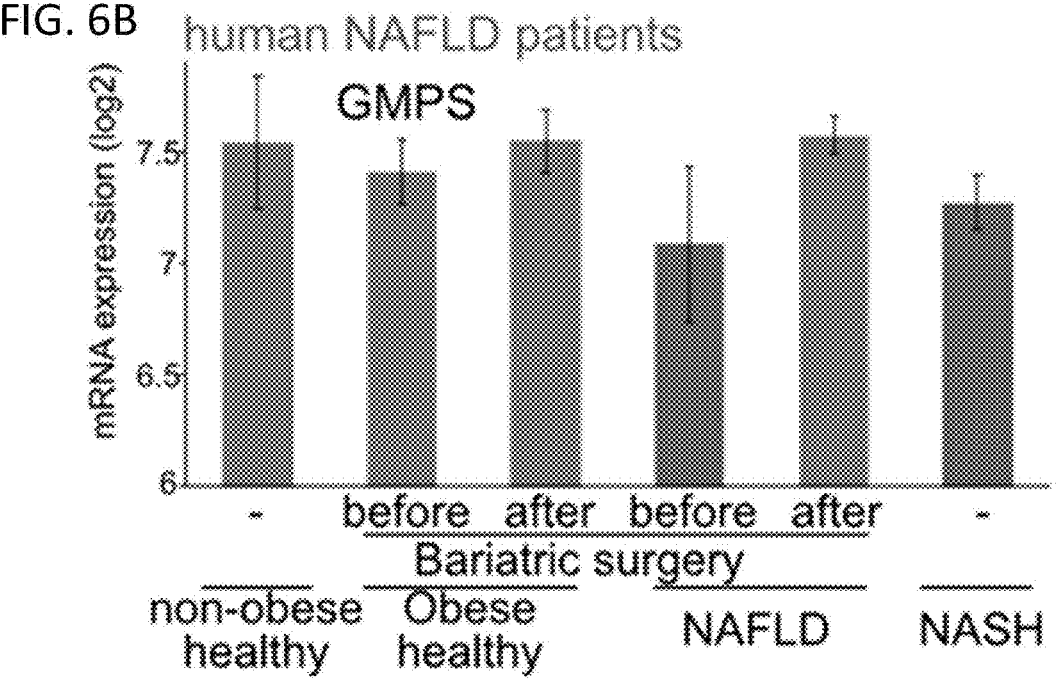

METHOD FOR THE DETECTION OF DRUG-INDUCED ORGAN OR TISSUE INJURY IN IMPDH INHIBITOR TREATED PATIENTS

RELATED APPLICATIONS

The present application claims priority to U.S. Provisional Patent Application 63/088,106, filed Oct. 6, 2020, which is hereby incorporated by reference in its entirety.

GOVERNMENT SUPPORT

This invention was made with government support under R01NS089815 awarded by National Institutes of Health. The government has certain rights in the invention.

TECHNICAL FIELD

This disclosure relates to a method for the detection, assessment, and/or diagnosis of organ or tissue injury. More specifically, the present invention relates to combination of methodology and biomarker that can be used in the detection, assessment and/or diagnosis of drug induced organ or tissue injury particularly in the setting of patients receiving treatment with IMPDH inhibitors and/or GMPS inhibitors.

BACKGROUND

In the pharmaceutical field, adverse drug reactions (ADRs) are a major clinical concern and are a significant cause of attrition in drug development.

Hepatotoxicity is a particularly prominent cause of drug attrition. As a primary organ for metabolism of administered drugs, the cells of the liver are vulnerable. The metabolism of drugs to chemically reactive metabolites in the liver is an important factor in drug-induced liver injury (DILI). However, the cellular events that link the chemistry of drug bioactivation to the toxicological outcome are poorly understood. A better understanding of the mechanisms and pathways leading to DILI would improve clinical management and inform the design of safer medicines for use in the clinic.

In addition, many drugs can also be toxic to other organs and tissues, such as the skin (irritation, rashes etc.), lungs, kidneys and heart. In severe cases, this may lead to drug attrition or necessitate additional clinical management. A better understanding of the mechanisms and pathways leading to skin, lung, kidney and cardiac toxicity would also be beneficial.

Additionally, DILI frequently displays unclassifiable (nonspecific) pathologic changes. The diverse, often non-specific histologic patterns make it difficult for pathologists to establish practical diagnostic criteria for DILI.

The importance of biomarkers to accelerate the pace of drug development, reduce attrition and to be biologically informative in their own right is becoming generally acknowledged in the pharmaceutical field. The ability to easily detect selective biomarkers of apoptosis, necrosis and inflammation would have immense benefit for differentiating the underlying causes of organ injury, such as drug induced liver, skin, lung, kidney or cardiac injury, and will provide additional information to aid clinical intervention and to inform the development of safer drugs in the future.

There are a few biomarkers that are associated with organ injury, such as, for example, alanine aminotransaminase (ALT), which is associated with liver injury. However, the detection of these biomarkers does not reveal any information about the underlying mechanism or progression of the organ damage.

A need exists for improved methods for the detection and treatment of drug-induced organ or tissue injury.

SUMMARY

Accordingly, it is an object of the present disclosure to provide a simple and convenient approach to identify adverse response in an organ or tissue to administered therapeutics and to proceed with corrective treatments to prevent or reduce further damage. In some aspects, the present disclosure includes methods for detecting and/or assessing drug-induced organ or tissue injury, which is also sufficiently sensitive so as to enable the early detection of organ or tissue damage.

It is a further object to provide methodology that enables the underlying mechanisms and pathways contributing to drug-induced organ or tissue injury to be assessed.

The present disclosure provides a means for the detection, assessment, and/or diagnosis of organ or tissue injury particularly in the setting of IMPDH (inosine monophosphate dehydrogenase) inhibitor and/or GMPS (guanosine monophosphate synthetase) treated patients.

In some aspects, the present disclosure includes methods for preventing sustained injury to a tissue in a subject undergoing a drug regimen for tissue or organ transplantation through obtaining a tissue or organ sample from a transplanted tissue or organ in a subject at a first time point, then determining the presence of aberrant mitochondria in the tissue or organ sample, wherein the aberrant mitochondria in the tissue or organ sample signify injury to the transplanted tissue or organ and, then taking remedial action for the drug regimen to prevent further injury to the transplanted tissue or organ.

In some aspects, the methods may include determining the presence of aberrant nuclei in the tissue or organ sample. In other aspects, the method may include determining the presence of IMPDH2 (inosine monophosphateC dehydrogenase 2) in the tissue or organ sample. In further aspects, the method may include determining lysosomal activity in cells of the tissue or organ sample.

In some aspects, the tissue or organ sample is a liver or kidney sample. In further aspects, the subject is a liver transplant recipient. In some aspects, the subject is being treated with an IMPDH and/or a GMPS inhibitor. In some aspects, the subject may be a kidney transplant recipient. In some aspects, the subject may have an autoimmune disease or be receiving treatment for an autoimmune disease and/or disorder. In even further aspects, the subject is undergoing a treatment regimen with an IMPDH inhibitor, such as mycophenolate mofetil (MMF) or MPA. In some aspects, the IMPDH inhibitor is one or more of mycophenolate mofetil (MMF), mycophenolic acid (MPA), tiazofurin, ribavirin, VX-944, and/or FF-10501

In some aspects, the remedial action is to cease the drug regimen and/or changing to a different drug. In some aspects, the subject is changed to a drug regimen of one of prednisone, tacrolimus, sirolimus, everolimus, azathioprine, leflunomide, prednisolone, budesonide, and/or cyclosporine.

In some aspects, the methods may also include obtaining a second tissue or organ sample from the transplanted tissue or organ in the subject at a second time point different from the first time point.

In some aspects, the present disclosure concerns methods for preventing liver injury in a subject with a liver transplant and undergoing MMF therapy, through obtaining a liver sample from the transplanted liver in the subject at a first time point, then determining the presence of aberrant mitochondria in the liver sample, wherein the aberrant mitochondria in the liver sample signify injury to the transplanted liver, and then taking remedial action for the MMF therapy to prevent further injury to the transplanted liver.

In some aspects, the methods include determining the presence of aberrant nuclei in the liver sample and/or the presence of IMPDH2 in the liver sample and/or lysosomal activity in cells of the tissue or organ sample. In some aspects, the presence of IMPDH2 is determined in Kupffer cells of the liver sample.

BRIEF DESCRIPTION OF THE DRAWINGS

FIGS. 1A-1C depict three patients' laboratory and biopsy results along with the given medications. FIG. 1A depicts the first patient, FIG. 1B depicts the second patient and FIG. 1C depicts the third patient. Multiple biopsies were performed for elevated liver function tests (LFTs), and the diagnoses were generally consistent with low-grade acute cellular rejection (ACR) (RAI ranging 2 to 4), except the initial biopsy of the first patient with RAI of 5. Initial steroids lowered the LFTs in some degrees. However, abnormal LFTs persisted despite aggressive immunosuppressive therapy.

(FIG. 2C and FIG. 2D) electron micrograph (FIG. 2C: 8000×, FIG. 2D: 18,000×) and the untreated mouse livers and livers treated with MMF (FIGS. 2E1, 2E2, 2F1, and 2F2: FIGS. 2E1 and 2F1: H&E [400×]; FIGS. 2E2 and 2F2: electron micrograph [8000×]). In addition to the features categorized into mild ACR, the histology showed mild, nonspecific (unclassified) hepatocellular abnormalities (reactive changes, FIGS. 2A and 2B). EM revealed prominent mitochondrial pleomorphism (variability in size and shape) and crystalloid inclusions (FIGS. 2C and 2D), except for the biopsy taken before stating MMF in Case 3. Arrowheads indicate extremely large ones among the pleomorphic mitochondria. Histologically, the livers from the untreated (FIG. 2E1) and MMF-treated mice (FIG. 2F1) showed no recognizable differences. They had only minimal reactive changes with mild anionucleosis and granular cytoplasm. Ultrastructurally, hepatocellular mitochondria of the MMF-treated mice (FIG. 2F2) showed more pleomorphism (variability in size and shape) and lipid droplets compared with the livers from the untreated mice (FIG. 2E2). Arrowheads indicate large pleomorphic mitochondria and lipid droplets. ACR=acute cellular rejection; EM=electron-microscopic examination; H&E=hematoxylin & eosin; MMF=mycophenolate mofetil.

FIG. 6A shows that IMPDH2 and GMPS levels in livers of C57BL/6 mice w/wo an high-fat diet (HFD) for 21 weeks (GSE24031). FIG. 6B shows that GMPS levels in human livers (GSE48452).

DESCRIPTION

Figures 1, 1B:
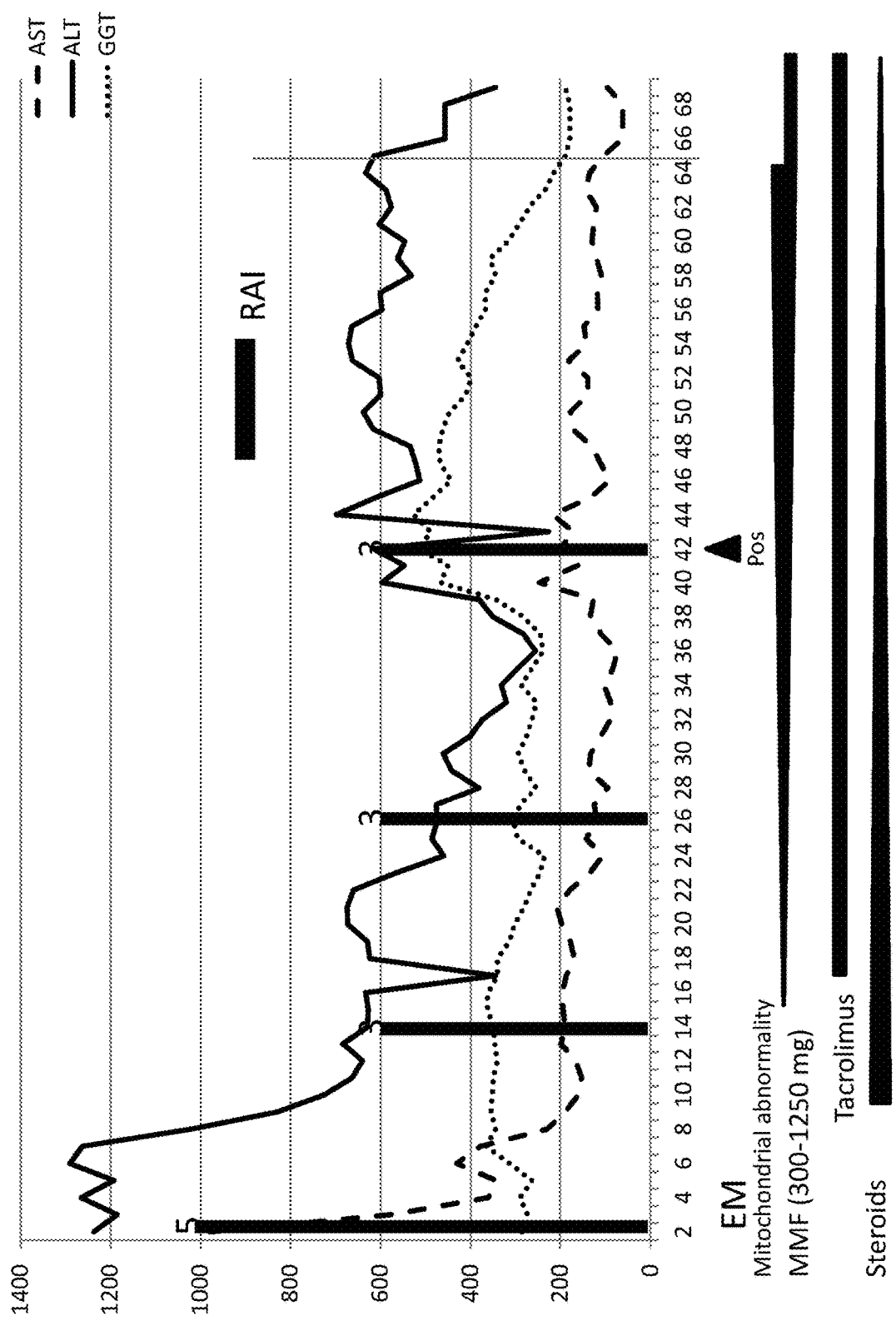

The present disclosure concerns methods to identify adverse responses to a therapeutic by a tissue or organ. In some aspects, the methods herein prevent injury or sustained injury to a tissue and/or organ of a subject. In some aspects, the identification of the adverse response allows for responsive action, such as the cessation of administration of the therapeutic, dosing changes to the amount of administered therapeutic, administration of one or more different therapeutics and/or lifestyle adjustments. In some aspects, the present disclosure may include one or more identification procedures for a subject undergoing a treatment regimen. In some aspects, the present disclosure may include monitoring one or more tissues and/or organs in a subject during a treatment course with one or more therapeutic agents.

In some aspects, the methods of the present disclosure concern the identification of adverse responses and/or reactions within one or more tissues or organs within a subject in response to a therapeutic. In some aspects, identification of one or more of the adverse responses within a subject allows a provider to adjust the therapeutic regimen, the dosing amount and/or the choice of therapeutic.

In some aspects, the methods of the present disclosure concern identification of an adverse response in a tissue or organ of a subject, where the subject is taking a therapeutic known or suspected of inhibiting IMPDH (inosine monophosphate dehydrogenase or inosine 5'-monophosphate dehydrogenase). IMPDH refers to a cellular enzyme that is responsible for the catalysis of IMP to XMP, which serves as a precursor to guanine nucleotides (e.g., guanosine triphosphate (GTP)). Typically, IMPDH inhibition is seen from administration of immunosuppressive compounds, antimicrobial compounds, or antiviral compounds. IMPDH inhibitors may in some aspects reversibly bind to and/or inhibit IMPDH. In other aspects, the IMPDH inhibitor may irreversibly bind and/or inhibit IMPDH. Examples include mycophenolic acid, mizoribine, ribavirin, C2-MAD, VX-497, AVN944, VX-148, BMS-337197, 1,5-diazabicyclo[3.1.0]hexane-2,4-dione, halicyclamine A, blastadin 11, 3-hydrogenkwadaphnin, 2264A, benzamide riboside, triciribine phosphate, oxanosine monophosphate, 1-AG-monophosphate, 3-deaza-guanine monophosphate, EICAR, 2-Cl-methyl-IMP, and 2-vinyl-IMP. In some aspects, the IMPDH inhibitor is the immunosuppressive compound, mycophenolic acid (MPA) and its prodrug form mycophenolate mofetil (MMF).

IMPDH immunosuppressants, such as MMF, are often administered to prevent and/or treat acute cellular rejection (ACR) in transplant recipients and to treat non-transplanted patients with various autoimmune disorders. MMF is an immunosuppressive agent commonly used to prevent and/or treat ACR in transplant recipients and to treat non-transplanted patients with various autoimmune disorders.

In some aspects, the subject may taking a GMPS inhibitor therapeutic agent. Guanosine monophosphate synthetase (GMPS) is one of three glutamine amidotransferases involved in de novo purine biosynthesis and is responsible for the last step in the synthesis of the guanine nucleotide, GMP. As identified herein, GMPS lies downstream of IMPDH activity in the production of GMP from inosine monophosphate with xanthosine 5'monophosphate (XMP) being the intermediate substrate in the pathway. Inhibitors of GMPS can include decoyinine and psicofuranine.

In some aspects, the subject may be the recipient of an organ transplant. In some aspects, the transplanted organ may be a liver. Transplant liver biopsy is routinely performed for abnormal liver function tests (LFTs). The indications are almost always to rule out acute cellular rejection (ACR) as it is the most common underlying diagnosis. Pathologists are well-trained to recognize ACR. However, other etiologies, often with nonspecific histology, are undervalued. MMF and/or MPA hepatotoxicity is thought to be rare and mild; only few sporadic cases are reported. The mechanism is unclear and the histologic/ultrastructural changes of MMF or MPA hepatotoxicity are not well-studied. As presented herein, four liver transplant patients presumed to have MMF-related hepatocellular injury demonstrated the injury to be associated with mitochondrial injury. To confirm, liver histology from MMF-treated and untreated mice is also herein discussed.

In some aspects, the present disclosure concerns obtaining a sample from a subject. In some aspects, the subject may be an organ or tissue transplant recipient. In some aspects, the organ may be liver, kidney, lung, skin, trachea, cornea, pancreas, heart, intestine, thymus, bone, tendon, heart valve, nerve, and/or vein/artery. In certain aspects, the subject is a liver transplant recipient. In other aspects, the subject is under assessment for organ and/or tissue injury. In some aspects, the present disclosure concerns obtaining a sample of tissue for the transplanted or organ under assessment. In some aspects, the sample is obtained by a biopsy.

In some aspects, the subject may be taking an IMPDH inhibitor and/or a GMPS inhibitor. In some aspects, the subject may be taking an IMPDH inhibitor and/or a GMPS inhibitor for immune suppression, such as with a transplanted organ or tissue. In some aspects, the subject may be suppressing an immune response due to an autoimmune disorder or suspicion thereof, such as lupus erythematosus, multiple sclerosis, type I diabetes, psoriasis, rheumatoid arthritis, inflammatory bowel disease (including Crohn's disease and ulcerative colitis), Addison's disease, Graves' disease, Sjorgen's syndrome, pernicious anemia, autoimmune vasculitis, celiac disease, and Hashimoto's thyroiditis.

In some aspects, the subject may be taking an IMPDH inhibitor and/or GMPS inhibitor for a cancer or a suspicion or diagnosis thereof. IMPDH inhibitors are actively being tested for treating various cancers due to IMPDH/GMPS's potential for tumor progression, such as through GMP production potential (see, Naffouje et al. Cancers (Basel) 2019 11(9): 1346).

In some aspects, the sample is obtained by percutaneous biopsy or aspiration, transjugular biopsy, laproscopic biopsy, endoscopic biopsy, fine-needle biopsy, core-needle biopsy, vacuum-assisted biopsy, image-guided biopsy, excisional biopsy, or surgical biopsy of an opening to excise a sample of the organ or tissue.

In some aspects, the present disclosure concerns identification of one or more subcellular and/or cellular responses that are indicative of an adverse response to the administration or presence of an IMPDH inhibitor, such as MMF and/or MPA. In some aspects, the methods include identification of mitochondrial morphology in a tissue or organ of a subject, such as by obtaining a tissue or cellular sample from the subject and observing the mitochondrial morphology therein. An aspect of the present disclosure is the identification that some subjects taking an IMPDH inhibitor, such as MMF and/or MPA, will respond adversely. In such instances, an early indicator of the adverse response is a change in mitochondrial morphology. Accordingly, monitoring the mitochondrial morphology for a subject taking an IMPDH provides an early indicator as to whether the IMPDH inhibitor will be harmful to the subject. In some aspects, the present disclosure concerns identification of mitochondrial abnormalcy as an indicator of early injury to a tissue and/or organ.

Observing mitochondrial morphology can be achieved through techniques understood in the art, including steps such as light and/or electron based microscopy, isolation of intact mitochondria, tissue fixation, tissue staining, and mitochondrial staining (e.g., antibody labelling, fluorescence labelling, tetramethylrhodamine, methy ester (TMRM) staining, Janus green B-dye staining, MitoTracker probes, or other commercially available labelling means). In some aspects, the observing mitochondrial morphology can be performed with a control, such as a known normal sample or a same from a different subject or a sample from a different tissue and/or organ from the same subject. In some aspects, mitochondrial morphology can be determined by measuring the cross-sectional width or length of mitochondria in the sample.

In further aspects, the nuclear morphology of nuclei in the sample can be observed. IMPDH has previously been identified to affect the morphology change the nucleolar morphology in metabolically active cells (Kofuji et al., Nature Cell Biology, 21: 1003-1014, 2019). The finding herein that IMPDH inhibitors can induce mitochondrial morphological changes and abnormality can be therefore coupled with observation of the nucleus to confirm the injury to the tissue and/or organ. In some aspects, the present disclosure concerns the observation and/or detection of nucleolar abnormality and mitochondrial abnormality by microscopic and immunobiological analyses to determine injury to the tissue and/or organ. In some aspects, the observation and/or detection of nucleolar abnormality and mitochondrial abnormality in a liver sample allows for an early determination of injury thereto. In certain aspects, the observation and/or detection of nucleolar abnormality and mitochondrial abnormality allows for the identification of MMF-induced DILI.

In some aspects, the methods provided herein may be used to predict, identify, observe and/or assess a patient's risk for hepatic injury in response to IMPDH inhibitors or GMPS inhibitors or an inhibitor suppressing GTP metabolism that have the ability to interact with or alter the expression or function of hepatic macromolecules leading to one or more hepatotoxic events, including but not limited to protein dysfunction, DNA damage, lipid peroxidation, oxidative stress, disruption of metabolite and ionic gradients, mitochondrial dysfunction, and the activation of innate and/or adaptive immune responses, in particular immune responses that are activated through the release of cytokine signals. The drug may interact with or alter the expression or function of hepatic macromolecules intrinsically or through bioactivation.

In some aspects, the present disclosure concerns detecting IMPDH2 expression in a tissue and/or organ sample. As identified herein, administration of an immunosuppressant, such as MMF leads to upregulation in cellular expression of IMPDH2. In some aspects, the sample is of a liver or a kidney from the subject. In some aspects, IMPDH2 expression is determined from a macrophage cell. In some aspects, IMPDH2 is measured in a Kupffer cell. In some aspects, IMPDH2 expression is determined in renal epithelial cells.

In some aspects, the methods of the present disclosure concern detection and/or measurement of lysosomal-related activities, such as lysosomal pH, lysosomal enzyme activities, autophagy, and autophagy-related phenomenon (e.g., mitophagy, ribophagy). In some aspects, the measurement and/or detection of lysosomal-related activities may report the status of IMPDH inhibition in the tissue and/or organ sample, such as a liver sample.

In some aspects, the methods of the present disclosure allow for an early determination of tissue and/or organ injury in a subject. In some aspects, the methods herein prevent injury or sustained injury to a tissue and/or organ of a subject. In some aspects, the methods of observing and/or detecting aberrant mitochondria in a sample from the subject allow for the determination that the tissue and/or organ is undergoing injury or receiving an injurious insult. In some aspects, the presence of aberrant nuclei along with aberrant mitochondria can confirm the injury to the tissue and/or organ. In some aspects, the observing and/or detecting of aberrant mitochondria confirm that an administered drug regimen is causing injury to the tissue and/or organ. In some aspects, the drug regimen is MMF to protect against an immune response to a transplanted tissue and/or organ. In some aspects, the subject is a liver transplant recipient receiving MMF to prevent against ACR.

In some aspects, the present disclosure concerns obtaining two or more tissue and/or organ samples from a same tissue or organ of a same subject, where the samples are obtained at different time points. In some aspects, the observing of mitochondrial and/or nuclear morphology can occur at multiple time points to assess or monitor the health of the tissue and/or organ. In some aspects, the present disclosure concerns monitoring the health of a tissue and/or organ by observing the morphology of the mitochondria and/or nucleus of the tissue or organ over the course of administration of a drug to the subject, such as an IMPDH inhibitor, such as MMF. In certain aspects, the present disclosure concerns monitoring the health of a transplanted tissue and/or organ by observing the morphology of the mitochondria and/or nucleus of the tissue or organ over the course of administration of a drug to the subject, such as an IMPDH inhibitor, such as MMF. In some aspects, the two or more time points can include observing a sample prior to initiation of a therapeutic regimen to obtain a baseline or starting point. In some aspects, the method may include obtaining a sample at the time of or shortly thereafter of a tissue and/or organ transplant, such as within about a month thereof, including about 4 weeks, 3 weeks, 2 weeks, 1 week, 6 days, 5 days, 4 days, 3 days, 2 days, and 1 day. In some aspects, a second time point for observing the mitochondrial and/or nuclear morphology of a sample of tissue and/or organ from the subject is of about a week, 2 weeks, 3 weeks, 4 weeks, 1 month, 2 months, 3 months, 4 months, 5 months, 6 months, 7 months, 8 months, 9 months, 10 months, 11 months, 1 year, 1.5 years, or 2 years from a prior sampling time point. In some aspects, the methods may including obtain 3, 4, 5, 6, 7, 8, 9, 10, or more tissue and/or organ samples from the subject at differing time points.

In some aspects, the present disclosure concerns methods to identify tissue and/or organ injury and to then act remedially. In some aspects, acting remedially can prevent and/or avoid significant injury to the tissue and/or organ. In some aspects, the remedial action can be to withdraw or cease administration of a drug, such as an IMPDH inhibitor, such as MMF and/or MPA. In some aspects, the remedial action may be switching to another IMPDH inhibitor. In such aspects, the method may including continuing to obtain samples of tissue and/or organ from the subject to monitor mitochondrial and/or nuclear morphology. In some aspects, the remedial action may include switching to a non-IMPDH medication, such as prednisone, tacrolimus, sirolimus, everolimus, azathioprine, leflunomide, prednisolone, budesonide, and/or cyclosporine. In some aspects, the remedial action may include surgery to resect necrotic tissue. In some aspects, remedial action may include administration of xanthosine monophosphate (XMP) to allow for production of guanosine monophosphate. In some aspects, the remedial action can include starting therapy with a biologic or antibody or fragment thereof to suppress the immune system of the subject. In some aspects, the present disclosure allows for remedial action to be taken to address or prevent further tissue and/or organ injury through the identification of aberrant mitochondrial and/or nuclear morphology in a sample obtained from a subject.

In some aspects, the present disclosure concerns methods to identify and remedy tissue and/or organ injury in a subject. In some aspects, the methods herein prevent injury or sustained injury to a tissue and/or organ of a subject. In some aspects, the subject is a recent transplant recipient. In further aspects, the subject is a liver transplant recipient. In some aspects, the subject is being administered an immunosuppressant for preventing organ rejection, such as an IMPDH inhibitor, such as MMF and/or MPA. In some aspects, the method includes a step of observing mitochondria from a tissue sample from the subject. In some aspects, the tissue sample is of a transplanted organ. In some aspects, the tissue sample is a transplanted liver sample. In some aspects, the mitochondria and/or nucleus are observed and/or measured for aberrance, such as enlargement. In some aspects, the methods include taking remedial action when aberrant mitochondria and/or nuclei are observed and/or detected. In some aspects, the remedial action may include drug cessation, drug replacement, surgery, further transplantation or similar. It will be appreciated that the remedial action is provided in response to the identification of the aberrant mitochondria and/or nuclei and without detection of at least the aberrant mitochondria, further tissue injury would progress, leading to increased necrosis and possible failure of a transplanted tissue and/or organ. It will also be appreciated that the methods of the present invention provide for early detection of tissue and/or organ injury, especially from an administered drug regimen, and that the methods disclosed herein allow for early remedial action that would not be achieved except for the methods herein allow for the early determination that remedial action is required.

Examples

Mycophenolate Mofetil (MMF)-Related Hepatocellular Injury Associated with Mitochondrial Abnormality in Transplant Patients and Mice Treated with MMF
Introduction:

Azathioprine, 6-mercaptopurine or cyclophosphamide, in combination with high-dose corticosteroids, were initially used for treating acute rejection in solid organ recipients in 1950-1960s. In 1980s, calcineurin inhibitors, such as cyclosporine and tacrolimus, were widely replaced the agents and enhanced the prophylactic roles. Mycophenolate Mofetil (MMF, CellCept®) and then sirolimus have emerged in 1990s. (Mukherjee et al. J Transplant. 2009;

2009:701464. doi: 10.1155/2009/701464. Epub 2009 Jul. 16. PubMed PMID: 20130772; PubMed Central PMCID: PMC2809333)

Drug-induced liver injury (DILI) can be associated with any of these immunosuppressive agents. However, the injury is thought to be generally mild and clinically significant cases were only rarely reported (Clinical and Research Information on Drug-Induced Liver Injury: NCBI bookshelf: www.ncbi.nlm.nih.gov/books/NBK547852/). It is often difficult to determine if particular immunosuppressive agents are the cause of the hepatotoxicity because these agents are often used with multiple other drugs and may be used in patients with pre-existing liver disease.

Transplant liver biopsy is routinely performed for transplant recipients when they have abnormal liver function tests (LFTs). Children's Hospital Los Angeles has one of the largest pediatric liver transplant centers in the US. Approximately 110-120 transplant liver biopsies are performed per year. The indications for biopsy are almost always to rule out acute cellular rejection (ACR) as it is the most common underlying diagnosis.

Pathologists are well-trained to recognize hepatitic patterns, particularly features of ACR. ACR is diagnosed according to the histologic criterion and grading system (Banff 1997). However, other etiologies of liver dysfunction, which often only show nonspecific hepatocellular injury, are undervalued.

DILI can be present with highly diverse histologic patterns, such as acute and chronic hepatitic patterns, cholestasis, combined cholestatic/hepatitic pattern, granulomatous inflammation, macrovesicular and/or microvesicular steatosis, steatohepatitis, various degrees of necrosis, and sinusoidal obstruction/veno-occlusive disease. In addition, DILI can frequently display mixed and unclassifiable injury or minimal nonspecific changes. (Fisher archive 2015) The diverse, often nonspecific patterns make difficult for pathologists to establish practical diagnostic criteria for DILI.

In transplanted livers, DILI have been much less commonly reported and reports describing histologic and ultrastructural findings are further rare. Due to the mild nonspecific presentations in many cases, diverse histologic patterns, and lack of criteria, DILI in transplant liver has been likely underestimated.

Herein are presented four liver transplant recipients, who were treated with MMF. Case 1-3 presented with persistent mildly elevated LFTs. Multiple biopsies showed features of "low-grade ACR", which was refractory to aggressive immunosuppressive therapy. Despite only mild nonspecific hepatocellular injury ("reactive changes") by histology, electron microscopy (EM) revealed unequivocal mitochondrial abnormality. In Case 1 and 2, LFTs improved after stopping or reducing MMF; therefore, MMF-related hepatocellular injury was suspected. For Case 3, pre- and post-MMF treatment biopsies were performed and only post-MMF treatment biopsy shows the similar mitochondrial abnormality. Case 4 treated with long-term MMF. She had normal LFTs but her surveillance biopsy showed the similar mitochondrial abnormality.

To confirm the hypothesis that MMF may have induced the mitochondrial abnormality, we reviewed histology and ultrastructure in livers from MMF-treated and untreated mice.

This is the first study describing the histologic and ultrastructural features of the livers from MMF-treated human patients and mice.

Case Reports:

Case 1-4 (3 females, 1 male; 3, 4, 13, 15 years) were treated with MMF. Case 1-3 presented with persistently elevated LFTs. Multiple biopsies showed features of "low-grade ACR" refractory to aggressive immunosuppressive therapy. Despite only mild nonspecific hepatocellular injury ("reactive changes") by histology, electron microscopy (EM) revealed mitochondrial pleomorphism and crystalloid inclusions. In Case 1 and 2, LFTs improved after stopping or reducing MMF; therefore, MMF-related hepatocellular injury was suspected. For Case 3, pre- and post-MMF treatment biopsies were performed and only post-MMF biopsy shows the similar mitochondrial abnormality. Case 4 treated with long-term MMF. She had normal LFTs but her surveillance biopsy showed the similar mitochondrial abnormality.

Mouse Study:

The livers were harvested from 3 MMF-treated (for 14 days, excluding 2 due to death) and 5 untreated mice. Histologically, MMF-treated livers showed minimal "reactive changes". Image analysis using EM revealed that the numbers of mitochondria and lipids and the degree of mitochondrial pleomorphism were significantly increased in the hepatocytes from the MMF-treated group compared with the untreated group.

Patients' Transplant Liver Biopsies:

Three patients (Case 1-3) had allograft liver biopsies in multiple times when the LFTs were elevated and/or did not successfully respond to the ACR treatments. One biopsy from a patient (Case 4) was performed for surveillance purpose.

Ultrastructural analysis included obtaining a small portion of the liver biopsies and post-fixing in osmium tetroxide and embedded in epoxy resin. Ultra-thin sections were stained with uranyl acetate/lead citrate. Detailed evaluation was made using Morgagni transmission electron microscope (EM, FEI, Hillsboro, OR).

2 H&E (hematoxylin and eosin) and 5 special (1 each for PAS, PASD, reticulin, iron and trichrome) stained slides were used per biopsy. ACR was diagnosed and scored using the Rejection Activity Index (RAI), which included: 1) portal inflammation (score 1-3), 2) bile duct damage (score 1-3), and 3) venous endothelial inflammation (score 1-3). Each score was added (RAI) and the degree of ACR was scored as follows: RAI=0-9; <3: borderline/indeterminate ACR, 3-4: mild ACR, 5-7: moderate ACR and >7: severe ACR. (Banff; 1997).

Nonspecific hepatocellular injury is often referred to "reactive changes". Histologic features of "reactive changes" include enlarged hepatocytes with hydropic changes (expanded, pale to clear cytoplasm) and coarse eosinophilic granules (e.g. mega-mitochondria), and nuclei with anisonucleosis and bi- and multi-nucleation, cholestasis, steatosis and necrosis. Necrosis can range from single cell necrosis (acidophil bodies) to rarely broad necrosis with collapsed lobules.

Mouse Liver Samples:

The body weights of the mice were recoded every day. Two mice in the MMF treated group died on day 12 and day 13 of the treatment and were excluded from the experiment. The rest of the mice were sacrificed on day 14 and a necropsy was performed on the surviving mice.

The liver was harvested and immediately fixed in 10% formalin (Medical Chemical Cooperation, Torrance, CA, USA) and 2.5% buffered glutaraldehyde (BCC Biochemical, Mount Vernon, WA, USA). H&E and trichrome staining was performed on each liver sections from 3 MMF treated and 5 untreated mice at a CLIA-certified laboratory at CHLA.

Ultrastructural analysis was performed as described for human liver biopsies on the mouse liver tissue from the MMF treated and untreated mice. The EM images were captured digitally at the same magnification (18,000×). Thirty hepatocytes per mouse liver are selected randomly and the numbers of the mitochondria and lipid droplets were counted per hepatocytes using the digital images. In addition, the greatest dimensions of randomly selected 50 mitochondria per hepatocytes from each mouse were measured using an image analysis software, Cellsens® (Olympus, Tokyo, Japan).

The numbers of the mitochondria and the lipid droplets and the sizes of the mitochondria of the hepatocytes from MMF treated and untreated mice were compared by repeated measures mixed model analysis, with patient as a random effect and group as fixed, at a 0.005 significance level, using Prism8 software (Graphpad Software, San Diego, CA, USA).

Results:

Case Reports:

Three female (4, 12 and 15 yo) and one male (13 yo) liver transplant recipients receiving MMF for the treatment of ACR presented with persistent mildly elevated LFTs. The patient's brief clinical demographics are summarized in Table 1.

Figures 1, 1C:
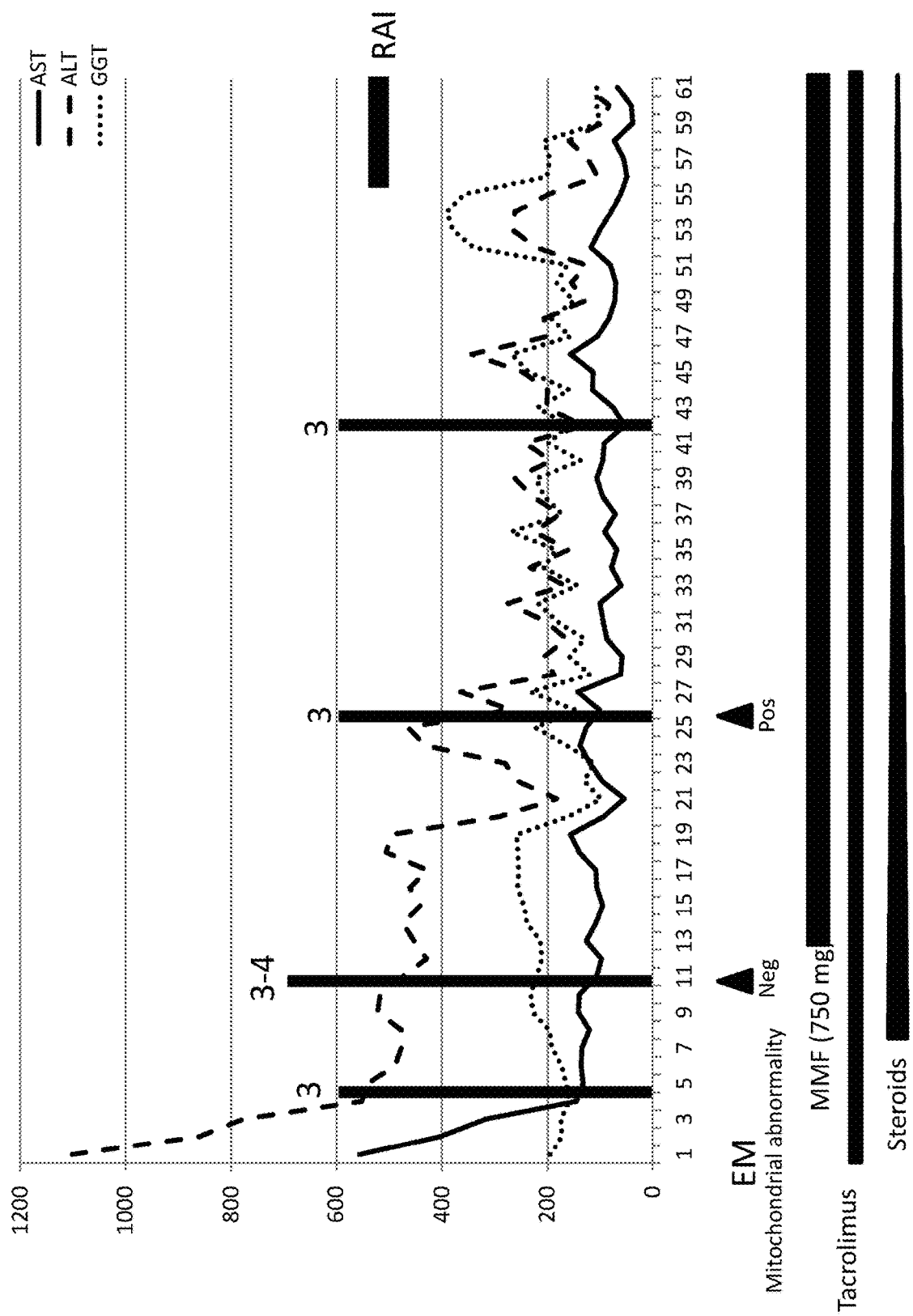

The patients' laboratory and biopsy results are shown along with the given medications in graphs (FIGS. 1A-1C). Multiple biopsies were performed for elevated LFTs, and the diagnoses were generally consistent with low-grade ACR (RAI ranging 2 to 4), except the initial biopsy of Case 1 with RAI of 5. Initial steroids lowered the LFTs in some degrees. However, abnormal LFTs persisted despite aggressive immunosuppressive therapy.

In Case 1 and 3, LFTs improved after stopping or reducing MMF; therefore, MMF hepatocellular injury was suspected. For Case 3, pre- and post-MMF treatment biopsies were performed and only the post-MMF treatment biopsy shows similar mitochondrial abnormality. Case 4 was treated with long-term MMF. She had normal LFTs but her surveillance biopsy showed similar mitochondrial abnormality.

Figure 2:
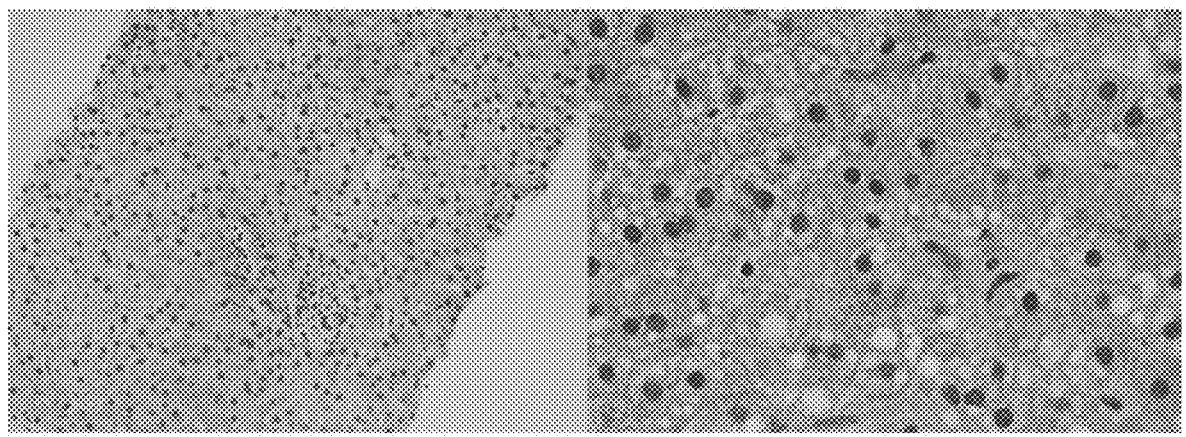
FIG. 2 depicts histologic and ultrastructural features of the transplant biopsies (FIG. 2A and FIG. 2B) H&E (FIG. 2A: 100×, B: 400×)
Figure 2:
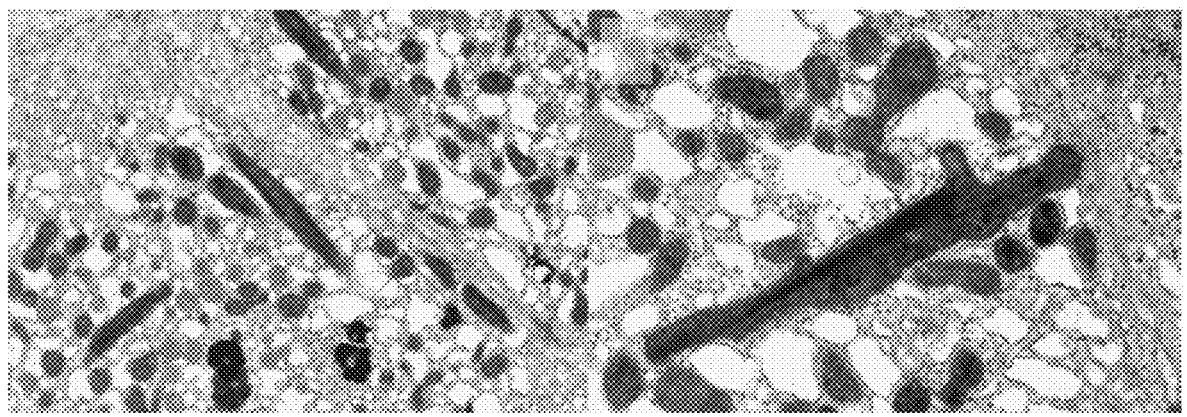
Figure 2:
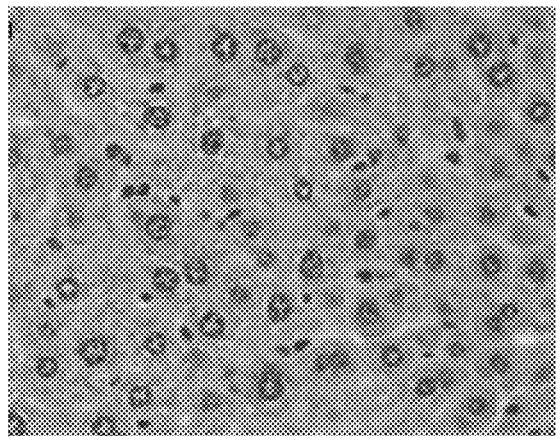
Figure 2:
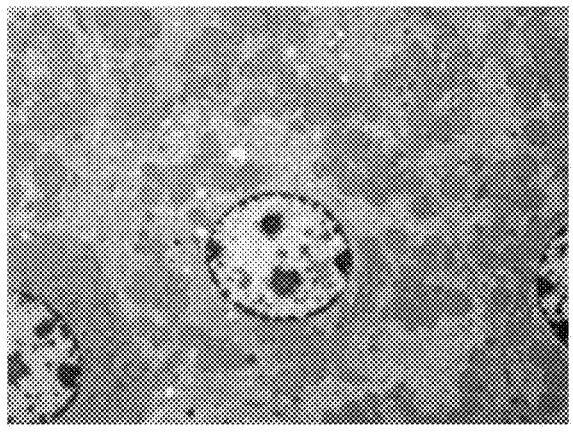
Figure 2:
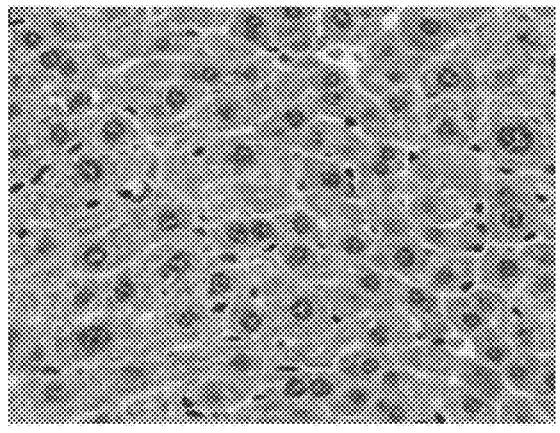
Figure 2:
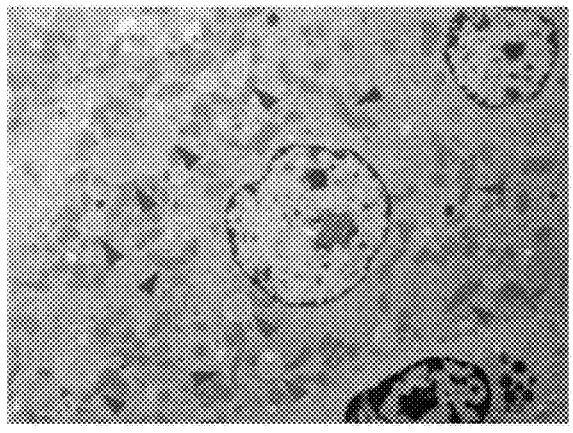

Patients' Transplant Liver Biopsies:

The histologic findings of each case were summarized in Table 1. In addition to the features of ACR including mild, patchy portal inflammation with or without mild ductal damages and/or mild subendothelial lymphocyte infiltrates, the histology showed only mild nonspecific hepatocellular injury ("reactive changes"). The "reactive changes" included mildly enlarged hepatocytes with granular cytoplasm, anisonucleosis, and focal areas with predominantly microvesicular-sized steatosis (FIG. 2). EM revealed mitochondrial pleomorphism and crystalloid inclusions. (FIG. 2).

| Case | Age/Sex | Time After Tx | Reason for Tx | Biopsy # | Time from initial biopsy | EM | RAI |
|---|---|---|---|---|---|---|---|
| 1 | 13 y/F | 2 mo | BA, failed Kasai | 1 | 0 | N | 3 |
|   |   |   |   | 2 | 8 day | N | 2 |
|   |   |   |   | 3 | 20 day | Y- mitochondrial pleomorphism | 2 |
| 2 | 4 y/F | 2 mo | Hepatoblastoma | 1 | 0 | N | 5 |
|   |   |   |   | 2 | 12 day | N | 3 |
|   |   |   |   | 3 | 25 day | N | 3 |
|   |   |   |   | 4 | 42 day | Y- mitochondrial pleomorphism inclusions | 3 |
| 3 | 17 y/M | 3 mo | CDG | 1 | 1 day | N | 3 |
|   |   |   |   | 2 | 6 day | Y- normal | 3-4 |
|   |   |   |   | 3 | 21 day | Y- mitochondrial pleomorphism, crystalloid inclusions | 3 |
|   |   |   |   | 4 | 37 day | N | 2 |
| 4 | 15 y/F | 13 y | BA, failed Kasai | 1 | 1 day | Y- mitochondrial pleomorphism, crystalloid inclusions | 2 |

| Case | Portal | Duct | Endothelial | Fibrosis | Lobular Inflammation | Addition features/testing |
|---|---|---|---|---|---|---|
| 1 | 1 | 1 | 1 | none | Rare mild | N/A/C4d negative |
|   | 1 | 1 | 0 | none | Focal nneutrophilic inf | N/A/viral study (CMV, EBV, HSV, and HSV neg) |
|   | 1 | 1 | 0 | Focal mild peisinusoidal and periportal | Minimal scattered | Diffuse reactive changes, mild sinusoidal dilatation/C4d negative |
| 2 | 2 | 1 | 2 | None | Occasional mild | N/A/CMV, adeno, HSV1/2. EBV neg |
|   | 1 | 1 | 1 | None | Rare mild | N/A |
|   | 1 | 1 | 1 | Mild periportal (stage 1) | Scattered single cell necrosis | N/A/CMV, adeno, HSV1/2. EBV neg |
|   | 1 | 1 | 1 |   | None | Ractive changes with lipofuscin, mild sinusoidal dilatation/CMV EBER neg, C4d neg |

-continued

| | | | | | | |
|---|---|---|---|---|---|---|
| 3 | 1 | 1 | 1 | Mild portal fibrosis (stage 1) | Rare mild | N/A/CMV, adeno, HSV1/2, EBER neg, C4d neg |
| | 1-2 | 1 | 1 | Perisinusoidal fibrosis (stage 0) | None | Mild zone 3 dilatation/C4d neg |
| | 1 | 1 | 1 | Perisinusoidal fibrosis (stage 0-1) | None | Diffuse reactive changes/C4d neg |
| | 1 | 1 | 1 | None | None | Reactive changes and scattered acidophil bodies/CMV, adeno, HSV1/2, EBER neg, C4d neg |
| 4 | 1 | 0 | 1 | Portal, perisinusoidal with focal bridging (stage 2-3) | None | Microvesicular steatosis (30%)/EBER neg |

Figures 3, 3A:
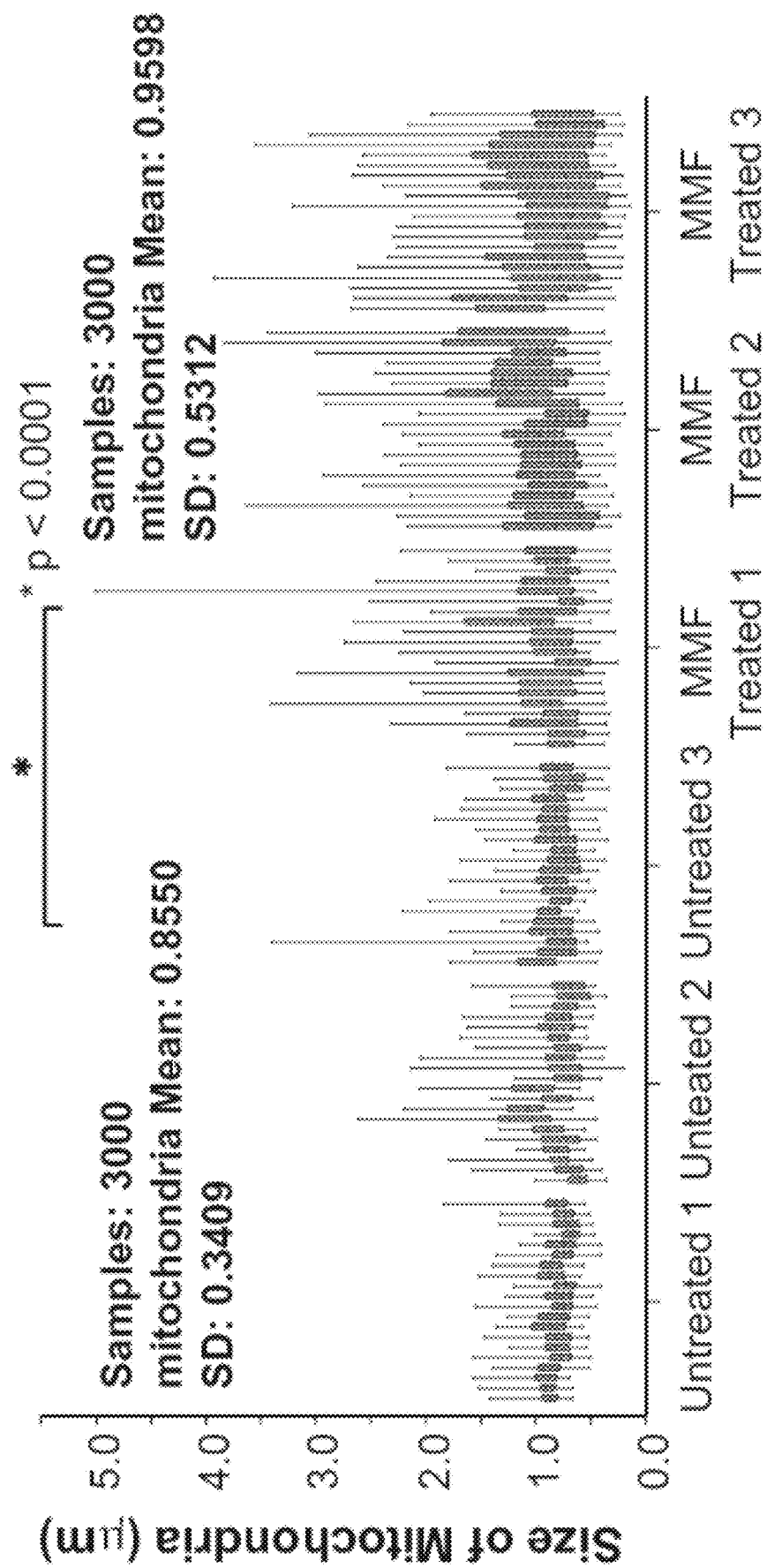
FIG. 3 depicts EM analysis of MMF-treated and untreated mice, revealing mitochondrial "stress changes" and the size of mitochondria (FIGS. 3A and 3B); the numbers of mitochondria (FIG. 3C) and lipids (FIG. 3D and the degree of mitochondrial pleomorphism (size differences) were significantly increased in the hepatocytes from the MMF-treated group compared with the untreated group.
Figures 3, 3D:
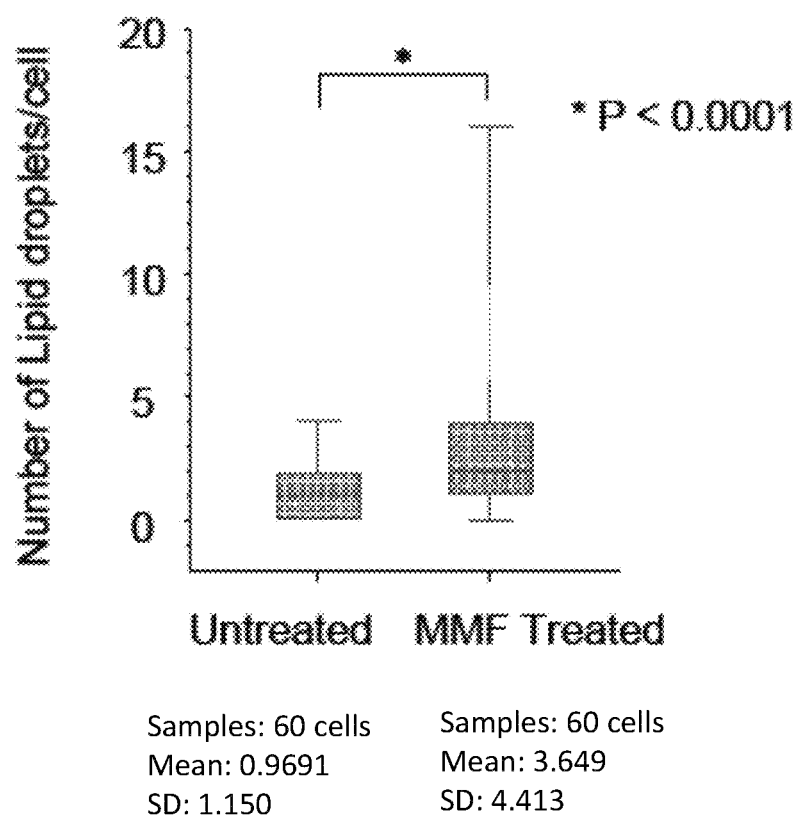
Figure 4:
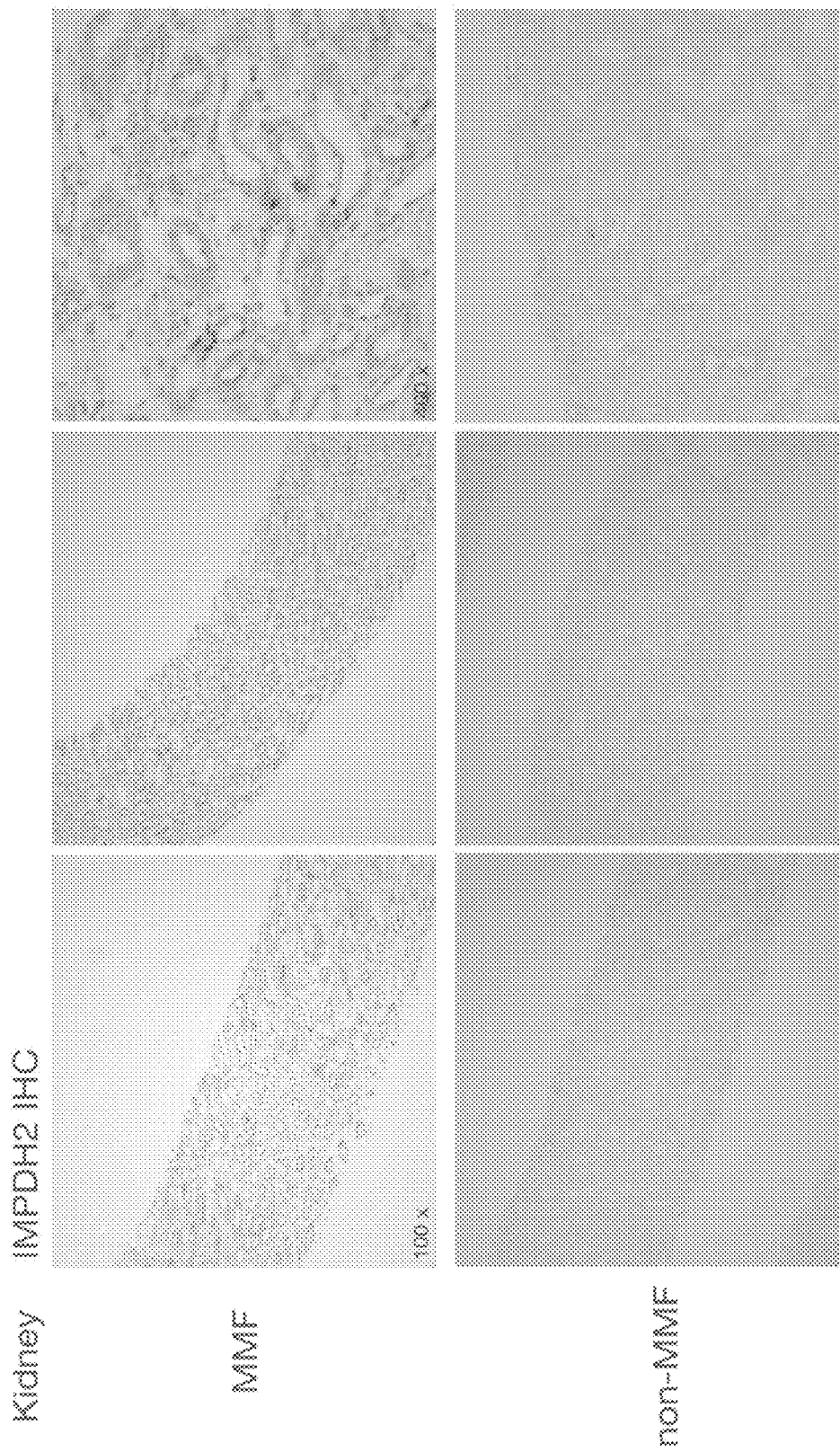
FIG. 4 depicts that reactive MMF-treated patient organ may increase in IMPDH2 upregulation. Immunohistochemical analysis using IMPDH2 specific antibody shows that IMPDH2 upregulation in patients treated with MMF for kidney transplantation who has a sign of rejection or undesired immunoreacted response.

Mouse Study:

The livers were harvested from 3 MMF-treated (for 14 days, excluding 2 due to death) and 5 untreated mice. Histologically, the livers from MMF-treated and untreated mice showed no recognizable differences. They show only minimal "reactive changes" with mild anionucleosis and granular cytoplasm (FIG. 3). Image analysis using EM revealed mitochondrial "stress changes"; the numbers of mitochondria and lipids and the degree of mitochondrial pleomorphism (size differences) were significantly increased in the hepatocytes from the MMF-treated group compared with the untreated group (FIG. 4).

Discussion:

The mouse study indicates that MMF caused mitochondrial "stress changes" in the hepatocytes. Similar changes may occur in humans. MMF is safe to use for the majority of patients but this "stress" may have further triggered the mitochondrial abnormality in a small subset of patients, who are possibly more susceptible to mitochondrial injury. MMF-related hepatotoxicity should be considered for any MMF-treated patients with unexplained abnormal LFTs and nonspecific histology. Since the histologic features are often subtle and nonspecific, EM would play a critical role in these cases.

Mycophenolate Mofetil (MMF, CellCept®) is a potent inhibitor of inosine monophosphate dehydrogenase-2 (IM-PDH2), the rate-limiting enzyme that regulates de novo guanosine triphosphate (GTP) biosynthesis. The depletion of GTP by MMF use has an anti-proliferative effect on lymphocytes since they depend on the de novo pathway for GTP synthesis. (Allison et al. Ann NY Acad Sci 1993; 696: 63).

MMF is, therefore, a powerful immunosuppressive agent widely used to treat various autoimmune diseases (e.g. systemic lupus erythematosus, pemphigus vulgaris, chronic idiopathic urticaria, myasthenia gravis, polymyositis, atopic dermatitis, Sjögren's disease, uveitis and vasculitis), autoimmune hepatitis, glomerulonephritis, and rejection in solid organ (heart, kidney and liver) and bone marrow transplant recipients. (Butani et al. Transplantation. 1999 Jul. 15; 68(1):83-6).

MMF hepatotoxicity (elevated LFTs) is thought to be rare. (Chalasani et al. Gastroenterology. 2008; 135:1924-34). Only a small number of sporadic cases has been reported in patients treated with MMF including patients with focal segmental glomerulosclerosis, atopic dermatitis, ANCA-positive vasculitis and scleritis (Sen. Ophthalmology 2003 September; 110(9):1750-5). Other reported 79 renal transplant recipients treated with MMF. Of these 11 patients (13.9%) had elevated LFTs (U/L), median and range of 83.0 (50-123) and 222.0 (51-508) of AST and ALT, respectively and abnormal LFTs were normalized after reduction or withdrawal of MMF. (Hernández Ann Hepatol. 2014; 13:231-9). The mechanism is unclear and the histologic and ultrastructural changes related to MMF hepatotoxicity have not been well-studied.

Mitochondria play a major role in cell-energy production through fatty acid oxidation, pyruvate oxidation and ATP formation by oxidative phosphorylation system. Mitochondria also have important role in cell death, which is triggered by mitochondrial membrane disruption (MMD). Therefore, mitochondrial damage can play an important role in hepatocellular injury in DILI. Hepatotoxic drugs are known to cause mitochondrial dysfunction through diverse mechanisms, such as directly inhibition of mitochondrial respiration and/or beta-oxidation of fatty acids and damage mitochondrial DNA (mtDNA), mitochondrial transcripts or mitochondrial protein synthesis (Pessayre 2012; more references required).

Histology of mitochondriopathies (including primary and secondary forms) is nonspecific and diverse, ranging from normal histology, reactive changes, hepatitic pattern, to various degrees of necrosis (Warren et al. Pediatr Dev Pathol. 2018 July-August; 21(4):347-354; Warren et al. Ultrastruct Pathol. 2018 May-June; 42(3):220-227). However, EM reveals significantly increased or, sometimes, decreased number of mitochondria, pleomorphism (increased variability in size and shape), cristae abnormalities often with "parking lot-like" crystalloid inclusions and cystic degeneration, and condensed matrix. In this study, EM played an important role to detect mitochondrial abnormality that was not detected by microscopic examination with routine H&E and special stains.

In summary, this is the first study describing the histologic and ultrastructural features of the livers from MMF-treated human patients and mice. The mouse study indicates that MMF caused mitochondrial stress changes in the hepatocytes. Similar changes may occur in humans (further study is awaited). MMF is safe to use for the majority of patients but stress changes may have further triggered the mitochondrial abnormality in a small subset of patients, who are possibly more susceptible to mitochondrial injury.

MMF-related hepatotoxicity should be considered for any MMF-treated patients with unexplained abnormal LFTs and nonspecific histology. Since the histologic features are often subtle and nonspecific, EM would play a critical role in these cases.

Reactive MMF Treated Patient Organ Increases IMPDH2 Expression Levels.

Figure 5:
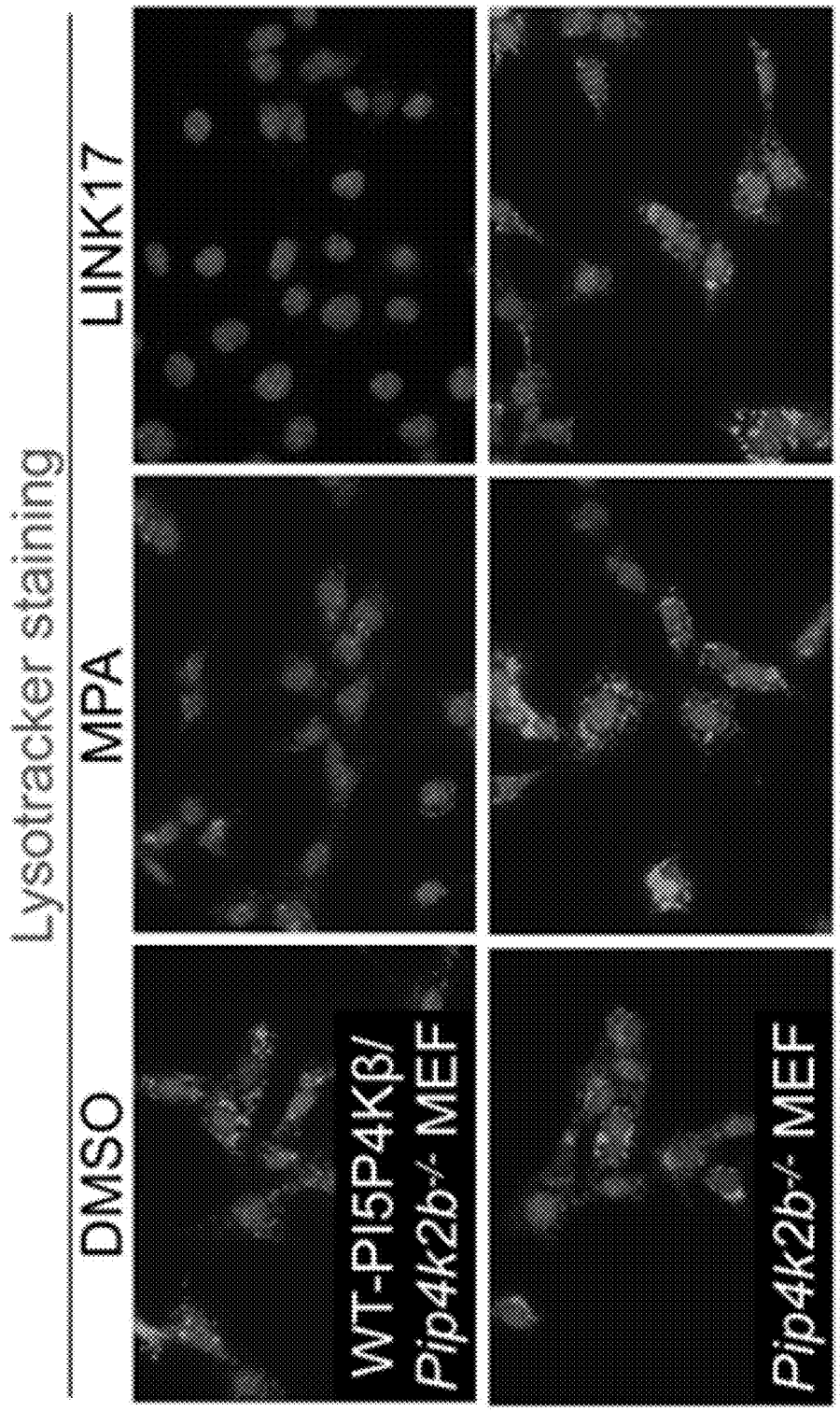
FIG. 5 shows that treatment of MPA for 2 h suppressed lysosomal acidification in serum starved WT-PI5P4Kβ/Pip4K2b$^{-/-}$ cells, but not in its isogenic Pip4K2b$^{-/-}$ cells. PI5P4K inhibiting compound LINK17 also suppressed lysosomal acidification in PI5P4Kβ-dependent manner.

Using a validated anti-IMPDH2 antibody, it was found that reacting kidney of the kidney patient treated with MMF significantly increases the IMPDH2 expression, particularly in the renal epithelial cells (FIG. 5). In many cells, the IMPDH2 signals are detected as speckles or dots in the cytoplasm of renal epithelial cells of the MMF-treated patients. In contrast, MMF non-treated patient specimens did not show such IMPDH2 expression. This is the first evidence that MMF-treatment is associated with the upregulation of IMPDH2 in the transplanted tissue. The results suggest that detection of IMPDH2 protein levels and localization in tissues provide a novel mean to assess the reactivity of tissue against IMPDH inhibitor.

Hepatic Kupffer Cells are Activated and Increased IMPDH2 Expression After MMF Treatment.

Importantly, it was found that using human liver specimens from MMF-treated patients also showed a significant increase in the number and size of macrophages in livers (Kupffer cells). To further study the potential changes caused by MMF treatment, an animal model (mouse) was used and treated with MMF 120 mg/kg daily for over two weeks by oral gavage. As a control, another group of mice was treated with the vehicle used for MMF. Among the issues investigated (e.g., liver, kidney, ovary, brain, white adipose and brown adipose tissues, pancreas, stomach, lung), a major change that is easily detected by light microscope (400× magnification) is pointed on hepatic Kupffer cells. In MMF treated mice, Kupffer cells were enlarged (hyperplasia/activated) and increased in their numbers. In addition, IMPDH2 expression levels within the Kupffer cells were increased compared to MMF-untreated mouse liver. Given that the other tissues did not show any significant changes by the standard light microscopic analysis, our new data suggest that assessing the numbers and morphological changes of and IMPDH2 expression levels in Kupffer cells provide an indirect means to the reactivity of MMF.

Pathogenic Signature of the Molecular Changes by IMPDH Inhibition.

The liver exhibits a large capacity for protein and lipid degradation. The half-life of hepatic proteins is known as the shortest among the tissues. There are two key lysosome-dependent digestive pathways vital for hepatic functions. Endocytosis promotes the degradation of blood circulating proteins (e.g., LDL, hormones) and lipids, which are uptaken and delivered to the lysosome. Autophagy is important for the clearance of accruing abnormal proteins, organelles, and lipid droplets (LDs) (lipophagy). The lysosome-autophagy system regulates hepatic insulin sensitivity, lipid metabolism, and protects hepatocytes from injurious stimuli (e.g., ROS) and the overactivation of inflammation. There is a general consensus in the literature that autophagy is downregulated in the fatty liver or liver with dysfunctions. Several independent cohort analyses showed the decreased autophagy in human liver injury associated with fat accumulation. Genetic- and high-fat diet-induced obese mice decrease macroautophagy (hereafter autophagy). Several mechanisms for the decreased autophagy in liver steatosis have been proposed. These include the decreased expression of autophagy and lysosomal genes, the reduction in a fusion of the autophagosome with the lysosome and the impaired lysosomal acidification. Among them, the impaired lysosomal acidification is a critical causative of the suppressed lysosomal hydrolase activity and has been found in the livers of human liver diseases patients and various murine liver injury models (e.g., high-fat diet (HFD), choline-deficient diet). Importantly, it was found that mycophenolic acid (MPA) treatment suppressed lysosomal acidification (FIG. 6). The result suggests that detection of lysosomal-related activities, such as lysosomal pH, lysosomal enzyme activities, autophagy, and autophagy-related phenomenon (e.g., mitophagy, ribophagy), may report the status of IMPDH inhibition in the livers or other tissues. Also, this phenomenon is also recapitulated in the cells treated with inhibitors for the GTP-sensor kinase PI5P4Kβ (LINK17), suggesting that MMF's dependent reactivity is achieved, at least in part, through the suppressed PI5P4Kβ activity by MMF-dependent GTP decrease (FIG. 6).

Suppression of GTP synthetic enzymes is associated with liver injury. Decades of studies using in vivo magnetic resonance spectroscopy (MRS) have shown that the livers of the liver injury (e.g., non-alcoholic fatty liver disease (NAFLD) and type II diabetes (T2D)) patients exhibit decreased stores and reduced replenishing rates of ATP. A caveat of those studies is that MRS cannot distinguish GTP from ATP signals, and all the detected nucleotide triphosphate (NTP) signals are assumed as ATP because of its predominance (about 80% of NTP). Given that the energy status of the ATP can be applied to other nucleotides, it is reasonably assumed that GTP energy metabolism is downregulated in injured livers. In line with this notion, a transcriptome analysis reveals decreased expression of the two key GTP synthetic enzymes—IMPDH2 and GMP synthetase (GMPS)—in mouse HFD-induced NAFLD model (FIG. 7). Also, data from human NAFLD and non-alcoholic steatohepatitis (NASH) patients indicates decreased GMPS expression, which is reversed by bariatric surgery (FIG. 7).

We claim:

1. A method for detecting injury to a tissue in a subject undergoing a drug regimen for tissue or organ transplantation, comprising:
   obtaining a tissue or organ sample from a transplanted tissue or organ in a subject at a first time point;
   determining the presence of aberrant mitochondria in the tissue or organ sample, wherein the aberrant mitochondria in the tissue or organ sample signify injury to the transplanted tissue or organ; and,
   taking remedial action to prevent further injury to the transplanted tissue or organ.

2. The method of claim 1, further comprising determining the presence of aberrant nuclei in the tissue or organ sample.

3. The method of claim 1, further comprising determining the presence of IMPDH2 (inosine monophosphate dehydrogenase 2) and/or guanosine monophosphate synthetase (GMPS) in the tissue or organ sample.

4. The method of claim 1, further comprising determining lysosomal activity in cells of the tissue or organ sample.

5. The method of claim 1, wherein the tissue or organ sample is a liver or kidney sample.

6. The method of claim 1, wherein the subject is a liver transplant recipient.

7. The method of claim 1, wherein the drug regimen comprises treatment with an IMPDH inhibitor.

8. The method of claim 7, wherein the IMPDH inhibitor is selected from the group consisting of mycophenolate mofetil (MMF), mycophenolic acid (MPA), tiazofurin, ribavirin, VX-944, or FF-10501.

9. The method of claim 1, wherein the remedial action is to cease the drug regimen.

10. The method of claim 1, wherein the remedial action is changing to a different drug.

11. The method of claim 10, wherein the subject is changed to a drug regimen of one of prednisone, tacrolimus, sirolimus, everolimus, azathioprine, leflunomide, prednisolone, budesonide, and/or cyclosporine.

12. The method of claim 1, further comprising obtaining a second tissue or organ sample from the transplanted tissue or organ in the subject at a second time point different from the first time point.

13. The method of claim 1, wherein the transplanted organ or tissue is liver and wherein the subject is undergoing a treatment regimen with mycophenolate mofetil (MMF) or mycophenolic acid (MPA).

* * * * *